United States Patent [19]

Boebel

[11] 4,282,884

[45] Aug. 11, 1981

[54] DEVICE FOR OBTAINING TISSUE SAMPLES

[75] Inventor: Manfred Boebel, Oetisheim, Fed. Rep. of Germany

[73] Assignee: Richard Wolf GmbH, Knittlingen, Fed. Rep. of Germany

[21] Appl. No.: 45,105

[22] Filed: Jun. 4, 1979

[30] Foreign Application Priority Data

Jun. 8, 1978 [DE] Fed. Rep. of Germany ... 7817220[U]

[51] Int. Cl.³ .............................................. A61B 10/00
[52] U.S. Cl. ...................................... 128/751; 128/754
[58] Field of Search ............... 128/751, 754, 755, 305, 128/310

[56] References Cited

U.S. PATENT DOCUMENTS

| | | | |
|---|---|---|---|
| 2,790,437 | 4/1957 | Moore | 128/751 |
| 3,995,619 | 12/1976 | Glatzer | 128/305 X |
| 4,011,869 | 3/1977 | Seiler, Jr. | 128/305 X |
| 4,167,944 | 9/1979 | Banko | 128/305 |

FOREIGN PATENT DOCUMENTS

| | | | |
|---|---|---|---|
| 1069398 | 5/1967 | United Kingdom | 128/751 |
| 249551 | 5/1970 | U.S.S.R. | 128/754 |

*Primary Examiner*—Kyle L. Howell
*Attorney, Agent, or Firm*—Kinzer, Plyer, Dorn & McEachran

[57] ABSTRACT

A device for obtaining tissue samples of the kind having tong-like handle members and in which a punch assembly provided with a distal recess and a cutting edge is axially extensible from a shaft and insertable in a tube provided with a counter cutting edge. According to the invention the punch assembly comprises a continuous distally closed tube which is axially movable in relation to a tubular receiver member for collecting punched-out tissue that is carried by said tube and loosely connected proximally to said shaft and closing off said shaft distally over at least a larger distal length, said punch assembly also being axially movable with respect to said shaft.

9 Claims, 5 Drawing Figures

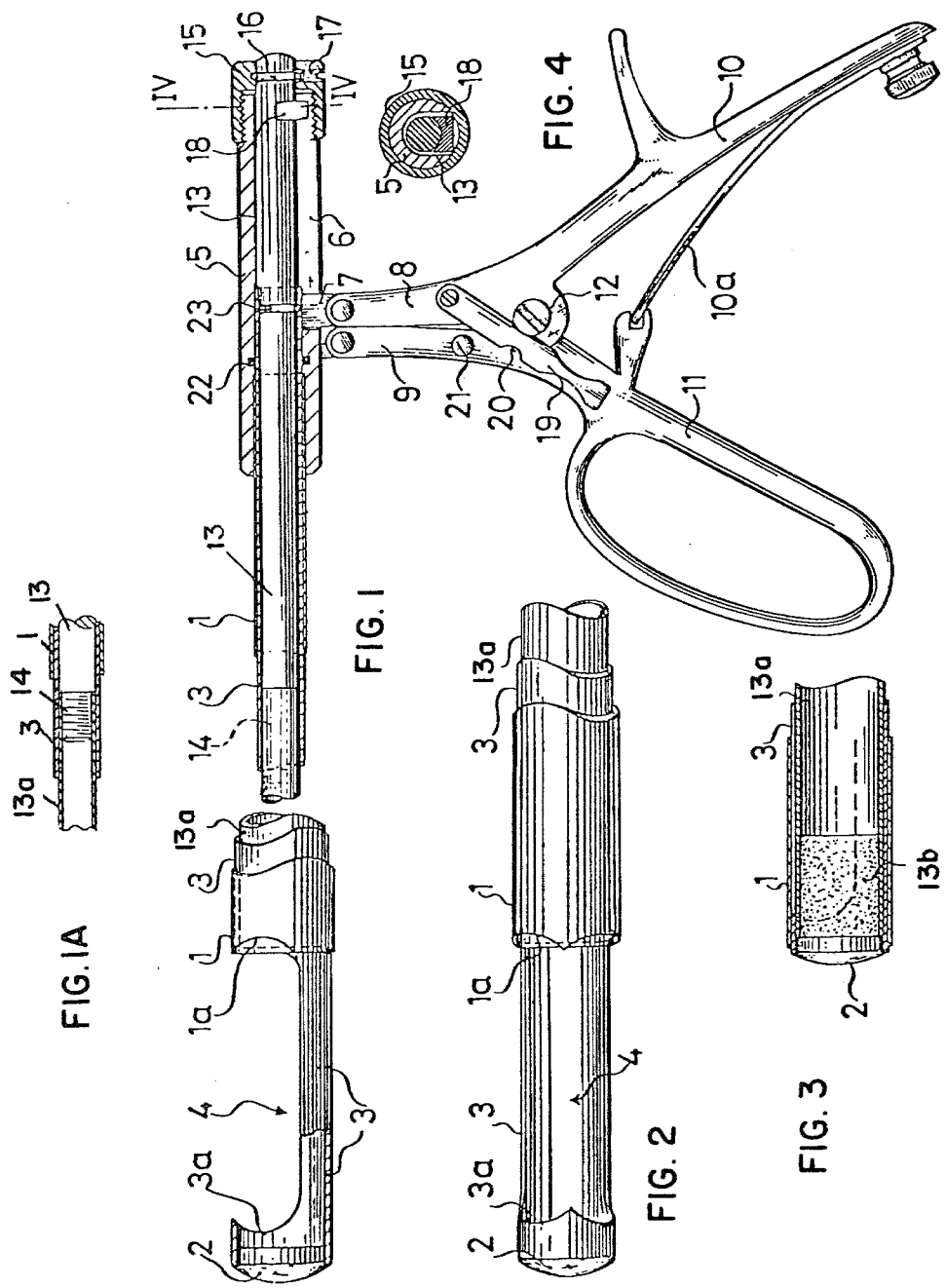

DEVICE FOR OBTAINING TISSUE SAMPLES

The present invention relates to devices having tong-like handles, for obtaining samples of tissue from the body, of the kind incorporating a punch assembly provided with a distal recess and a cutter. Such devices are used, for example in performing biopsies.

With known devices, often referred to as tissue punches of the above mentioned type, as exemplified by German Gebrauchsmuster No. 705342 it is necessary, every time the distal groove is filled with tissue, to remove the punch assembly together with the shaft from the field of operations through a trocar tube for example so as to remove the tissue and, then return the tissue punch to the operational area again.

It is an object of the invention to be able to remove the tissue after each or several perforation steps and to leave the shaft and the punch assembly in the operational area.

This and other objects are achieved by providing a device for obtaining tissue samples of the kind having tong-like handle members and in which a punch assembly provided with a distal recess and a cutting edge is axially extensible from a shaft and insertable in a tube provided with a counter cutting edge, which device consists in that said punch assembly comprises a continuous distally closed tube which is axially movable in relation to a tubular receiver member for collecting punched-out tissue that is carried by said tube and loosely connected proximally to said shaft and closing off said shaft distally over at least a larger distal length, said punch assembly also being axially movable with respect to said shaft.

With this construction, only the receiver member which catches the tissue which has been stamped out needs to be withdrawn in the proximal direction by disconnecting a proximal connection with the shaft so as to remove the tissue from the receiver member; this receiver member is then reinserted through the tubular punch assembly which has remained in the operational area with the shaft and is again connected up to the shaft for punching out more tissue.

BRIEF DESCRIPTION OF THE DRAWINGS

In order that the invention may be more clearly understood, reference will now be made to the accompanying drawings which show one embodiment thereof by way of example and in which:

FIG. 1 is a side view of the device in its operational position with the proximal portion in axial section and the distal end shown in side view to an enlarged scale and in part axial section, FIG. 1A is a detail view showing certain connections, FIG. 2 is a plan view of the distal end of the device to an even larger scale than that of FIG. 1, FIG. 3 is an axial section of the distal end of the device with the punch assembly retracted, and FIG. 4 is a cross-section along the line IV—IV of FIG. 1.

DETAILED DESCRIPTION OF THE PREFERRED EMBODIMENT

Referring now to the drawings, the device for obtaining samples of body tissue consists of an outer shaft 1 provided with a prong-shaped cutting edge 1a at its distal end in which a tubular punch assembly 3, which is closed at its distal end with a stopper 2 and providing a distal recess 4 having a prong-shaped counter cutting edge 3a, is axially displaceable. The shaft 1 is fixed proximally in a reinforcing housing 5 which has a longitudinal slot 6 in the side opposite the recess 4, through which projects a rectangular connecting piece 7 which is connected with the punch assembly 3. The shanks 8 and 9 which are pivotally connected to two handles 10 and 11 at 12 in the manner of tongs, pivotally connect respectively the connecting piece 7 and the housing 5 which receives outer shaft 1. The tong-like handles are forced by a spring 10a into an open position in which the connecting piece 7 of the shank 8 reaches the distal end of the slot 6 and in which position the punch assembly 3 with the recess 4 protrudes out of the shaft 1. Conversely, on closing the handles 10, 11 the punch assembly retracts into the shaft 1 due to the spreading of the tong shanks 8 and 9 until the distal end of the punch assembly 3 closes off the distal end of the shaft 1.

A receiver member 13 is proximally detachably connected to the reinforcing housing 5 and passes through the tubular punch structure 3, ending at the distal end of the shaft 1. The proximal end portion of the receiver member is a solid rod 13 and the distal end of this rod portion is screwed into a tubular portion 13a of receiver member 13, being open at its distal end. This screw connection is indicated with reference number 14 in FIG. 1. The rod portion 13 at the proximal end is detachably connected to the housing 5 by a cap nut 15. In order that the nut 15 can be screwed on to the housing 5 without turning the receiver member 13, the nut 15 and the receiver member 13 are each provided with an annular groove 16 in which a number of ball bearings have been inserted through a radial bore sealable by means of a grub screw 17 so that the nut 15 is rotatably connected to the receiver member 13 by a ball bearing and can be screwed onto the housing 5. The receiver member 13 is prevented from rotating by a wedge 18 which engages in the longitudinal slot 6 of the housing 5. However, if desired, the screw 14 and the nut 15 may have threads of opposite hand so that the nut 15 can be fixidly connected to the receiver member 13.

The medical tissue sample-obtaining device operates as follows. By pressing together the tong-like handles 10, 11, the shanks 8, 9 open, the punch assembly 3, 4 passes into the distal end of the shaft 1, as shown in FIG. 3, and in this position the handles 10, 11 are locked by a latch 19 which moves horizontally so that a recess 20 therein engages with a pin 21. The device is then inserted into a body cavity through a trocar housing for example. As the body cavity must be kept distended by a pneumoperitoneum in certain circumstances, the punch assembly 3 is kept sealed against the housing 5 by a ring 22 and the receiver member 13 is kept sealed against the punch assembly by a ring 23 and the punch assembly 3 is closed at its distal end by the stopper 2.

After insertion into the body cavity the whole latch assembly 19, 20, 21 is released so that the shanks 8, 9 approach the handles 10, 11 due to the spring 10a and thus the punch assembly 3 is pushed out of the shaft 1 into the position shown in FIG. 1. The recess 4 is now pressed against the tissue to be punched and the handles 10, 11 are pressed together so that a portion of tissue is punched out by the insertion of the punch assembly 3 into the shaft. Thus the tissue portion which is punched out is pressed into the distal tubular part 13a of the receiver member 13 where it is additionally held by an inner rough part 13b during removal of the punch assembly for a further punching operation. During successive punching operations, the tissue portions or samples are collected in the distal receiver portion 13a.

Finally the punch assembly 3 is pushed into the distal end of the shaft 1 again and secured by the latch assembly 19, 20, 21 and then the nut 15 is unscrewed from the housing 5 and the receiver member 13 is removed whilst the shaft and the punch assembly remain in the body cavity so as to remove the tissue collected from the receiver portion 13a, the screw coupling 14 of the receiver portion 13a advantageously being undone. Then the receiver portion 13a is again inserted and fastened in position by the nut 15 so that further punching operations can be carried out.

I claim:

1. In a device for obtaining medical tissue samples from an operating area and being of the kind having a scissors handle and an outer shaft joined to a reinforcing housing, in which a tubular punch structure, having a closed distal end and provided with a recess near the distal closed end and also having a cutting edge directed to the proximal end of the device, can be pushed axially out of the open end of the outer shaft, the outer shaft having a cutting edge opposite to the cutting edge of the punch structure, and which punch structure can also be drawn back into the outer shaft to engage the cutting edges thereby to remove tissue from the operating area, the improvement comprising:

a receiver member positioned inside the tubular punch structure and having an open end terminating near the distal end of the outer shaft, said receiver member comprising a length of a tubular receiving tube proximally connected detachably to a rod, and said rod being proximally detachably connected to the housing so that after tissue has been collected in the distal end of the tubular receiving tube the receiver member may be detached and separated from the housing allowing the remainder of the device to remain in the operational area.

2. A device according to claim 1, wherein said shaft is attached proximally at the distal end of a reinforcing housing the proximal end of which latter is detachably attached to the proximal end of said receiver member, said housing having a longitudinal slot for the passage of one of two scissors shanks pivotally attached to said punch structure, the other one of said two shanks being pivotally connected to said housing.

3. A device according to claim 2, wherein said receiver member is connectable to said housing proximally be means of a nut which is screwable onto the proximal end of said housing.

4. A device according to claim 3, wherein said nut and said receiver member are provided with opposed annular grooves in which several ball bearings are located.

5. A device according to claim 2, wherein said receiver member engages proximally in said longitudinal slot of said reinforcing housing by means of a wedge to prevent its rotation.

6. A device according to claim 2, wherein said tubular receiver member has a rod portion the proximal end of which is threadedly connected with a nut which in turn is screwable onto the proximal end of said reinforcing housing.

7. A device according to claim 2, wherein said tubular punch structure is sealed on the outside with respect to said reinforcing housing and on the inside with respect to said receiver member by means of sealing rings.

8. A device according to claim 1, wherein the interior of the distal end of said tubular receiver member is provided with roughened means.

9. A device according to claim 1, wherein the cutting edges are in the form of prongs.

* * * * *